United States Patent [19]

Biber

[11] Patent Number: 5,383,637
[45] Date of Patent: Jan. 24, 1995

[54] COUPLING FOR CONNECTING A SURGICAL MICROSCOPE TO A STAND

[75] Inventor: Klaus Biber, Aalen, Germany

[73] Assignee: Carl-Zeiss-Stiftung, Heidenheim

[21] Appl. No.: 132,904

[22] Filed: Oct. 7, 1993

[30] Foreign Application Priority Data

Oct. 8, 1992 [DE] Germany .................. 4233658

[51] Int. Cl.6 ............................................. E04G 3/00
[52] U.S. Cl. ........................................ 248/291; 359/384
[58] Field of Search ............... 248/291, 123.1, 289.1, 248/285; 403/92, 93; 359/384, 382

[56] References Cited

U.S. PATENT DOCUMENTS

| | | | |
|---|---|---|---|
| 1,548,238 | 8/1925 | Adams | 248/289.1 X |
| 2,711,300 | 6/1955 | Nelson | 248/291 X |
| 3,063,668 | 11/1962 | Yohe | 248/285 X |
| 4,881,709 | 11/1989 | Nakamura | 359/384 X |
| 5,168,601 | 12/1992 | Liv | 403/93 X |
| 5,197,817 | 3/1993 | Wood | 403/93 |
| 5,205,522 | 4/1993 | Nakmura | 359/384 X |
| 5,213,293 | 5/1993 | Muentener | 248/123.1 |
| 5,288,043 | 2/1994 | Tigliev | 359/384 X |
| 5,299,173 | 4/1994 | Bertrand | 248/289.1 X |

FOREIGN PATENT DOCUMENTS 2206152 12/1988 United Kingdom ............ 403/92

*Primary Examiner*—J. Franklin Foss
*Attorney, Agent, or Firm*—Walter Ottesen

[57] ABSTRACT

The invention is directed to a coupling for connecting a surgical microscope to a stand. The coupling permits different base positions for the surgical microscope to be set and includes a conical bearing which is held together by a spring packet. An indexing pin of a latching device engages the conical bearing for fixing a selected base position.

9 Claims, 3 Drawing Sheets

COUPLING FOR CONNECTING A SURGICAL MICROSCOPE TO A STAND

FIELD OF THE INVENTION

The invention relates to a coupling for connecting a surgical microscope to a stand. The coupling permits setting different base positions from which the surgical microscope is movable about a tilt axis and about a pivot axis.

BACKGROUND OF THE INVENTION

Tilting of the surgical microscope is a rotational movement about a tilt axis and pivoting is a rotational movement of the microscope about a pivot axis. The tilting movement is understood to be a movement forwardly or rearwardly and the pivoting is understood to be a movement to the left or to the right viewed from the position of the operator. The particular rotational range with respect to a preselected base position extends approximately ±30°. In order to align the surgical microscope in a larger spatial region with respect to the operating field, it is known to provide different base positions of the surgical microscope on the stand from which the microscope can be tilted and pivoted.

The setting of different base positions has not been improved in known apparatus in that the setting is either not free of play or the setting is limited with respect to the load that can be applied.

SUMMARY OF THE INVENTION

It is an object of the invention to provide a coupling for connecting a surgical microscope to a stand for setting different base positions which corresponds to the increased expectations of the surgeons.

The coupling of the invention is for connecting a surgical microscope to a stand so as to permit the microscope to be set in a plurality of base positions relative to the stand. The microscope has a carrier and is pivotable about a pivot axis in each of the base positions. The coupling includes: a supporting part for holding the carrier; a connecting part for connecting the coupling to the stand; the supporting part having a first bearing part and the connecting part defining a second bearing part; a holder for holding the bearing parts together to conjointly define a bearing and a bearing interface at which the parts rotate relative to each other; the holder including: a first member connected to one of the bearing parts; a second member engaging the first member for holding the bearing parts together to provide friction force at the interface; and, resilient biasing means interposed between one of the bearing parts and one of the members to determine the friction force; and, indexing means for indexing the microscope in any one of the base positions.

The advantages obtained with the invention are seen especially in that different base positions for the surgical microscope can be adjusted free of play so that the coupling ensures a high degree of reliability. Another advantage of the invention is that the coupling is economical to produce.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
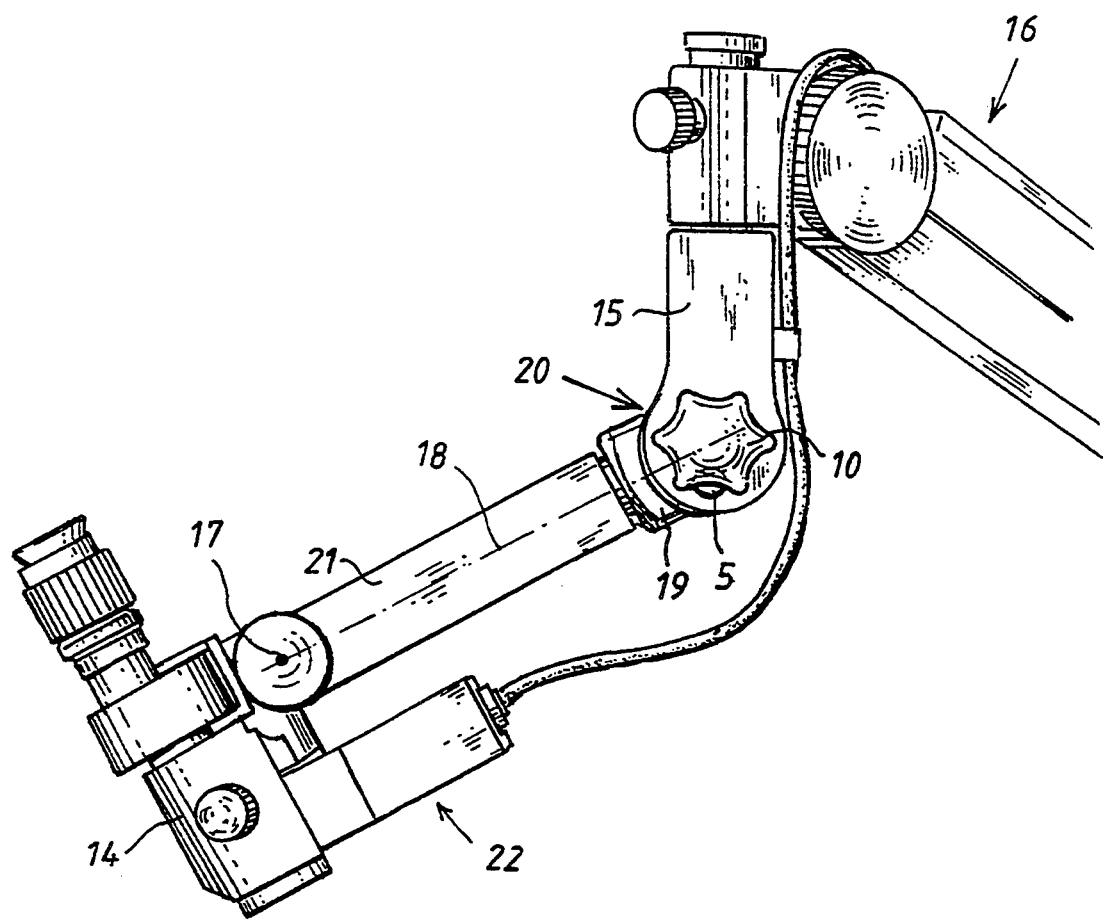
FIG. 1 is a perspective view of a surgical microscope connected to a stand with the coupling according to the invention.

FIG. 1 includes a stand 16 of which only a portion thereof is shown. The surgical microscope 14 is connected via a carrier 21 to the coupling 20 which, in turn, is connected via connecting part 15 to the stand 16. The surgical microscope 14 can be tilted about the axis 17 and be pivoted about the axis 18. Reference numeral 22 identifies an illuminating device as it is conventionally coupled to a surgical microscope.

Figure 2:
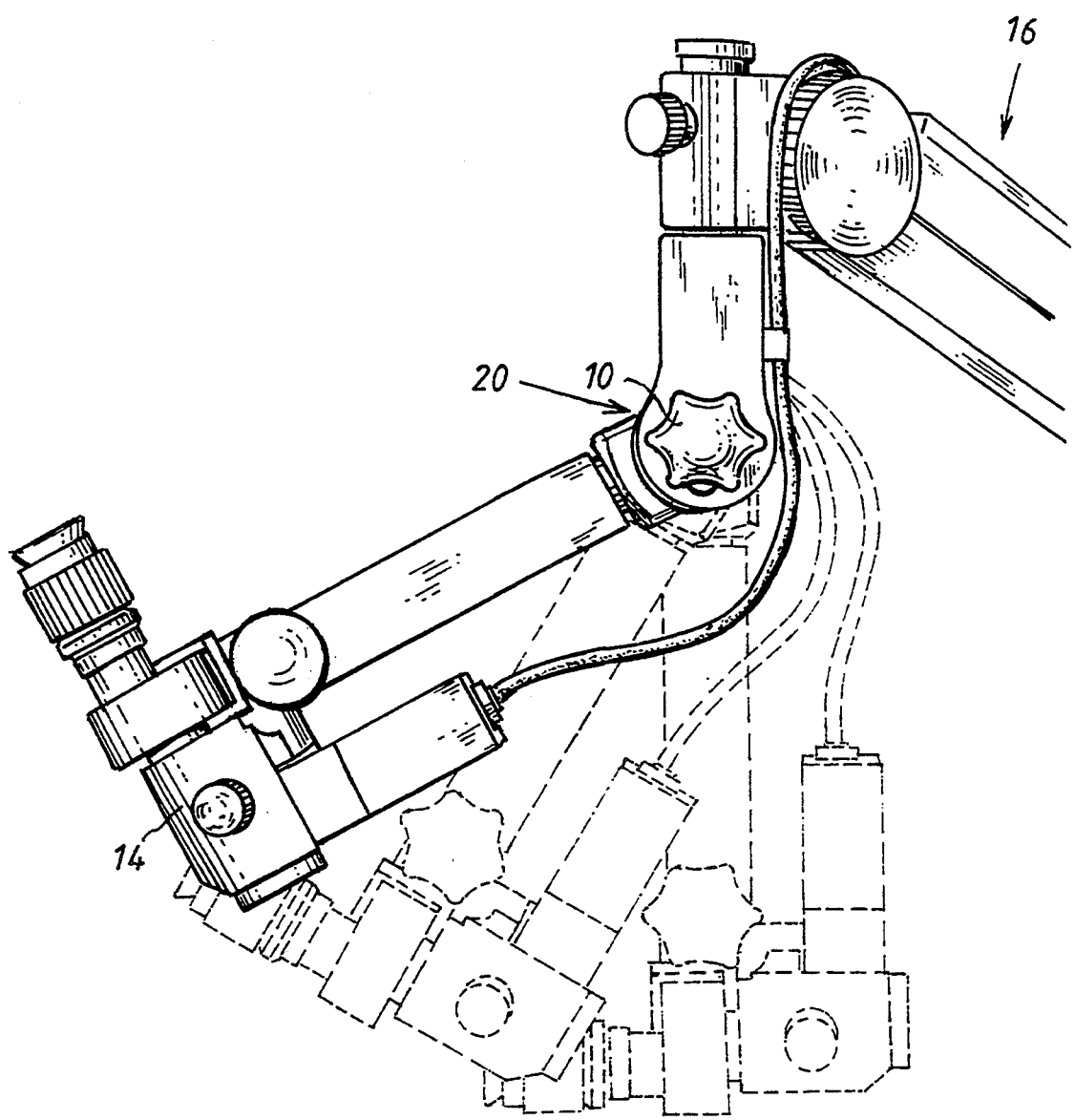
FIG. 2 corresponds to the view shown in FIG. 1 except that two additional base positions of the surgical microscope are shown in phantom outline; and, FIG. 3 shows the coupling for connecting the surgical microscope to the stand wherein a major portion of the coupling is broken away to show the elements of the coupling which coact to provide the base settings.

In FIG. 2, two further possible base positions are shown in phantom outline in addition to the base position shown in FIG. 1 for the surgical microscope 14.

Figure 3:
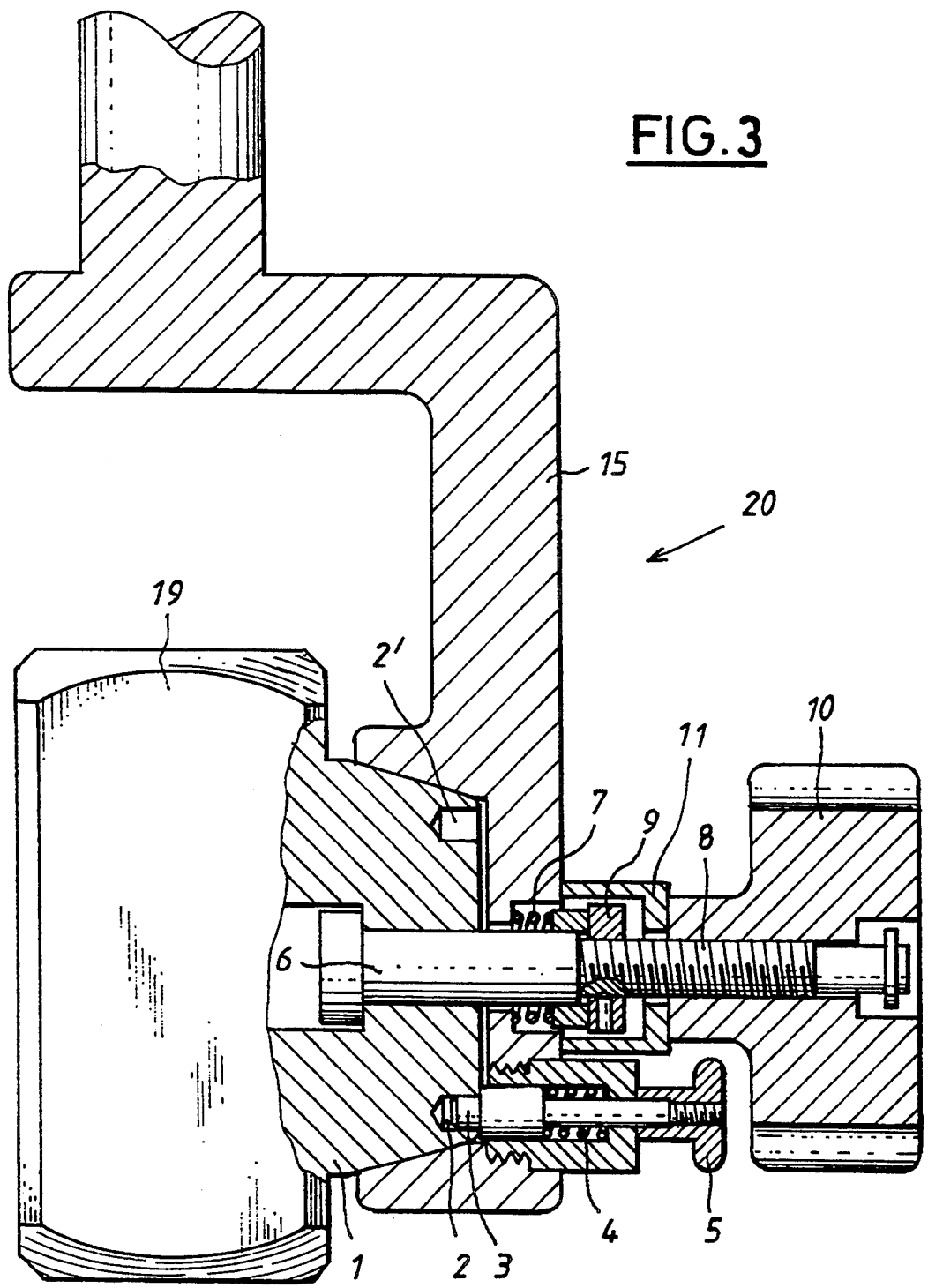

The assembly of the coupling for connecting the surgical microscope 14 to the stand 16 is shown in FIG. 3. The truncated conical portion 1 is journalled in the connecting part 15 and includes bores (2, 2'). The number of bores is not necessarily limited to the two shown; rather, as many bores can be provided in the truncated cone 1 as there are base positions desired for the surgical microscope 14. A receptacle 19 is provided for the connection of the carrier 21 to the coupling. A shaft 6, a spring 7, a thread 8 and an adjusting nut 9 are parts of a spring packet which holds together the conical bearing 1, the part defining the receptacle 19 and the connecting part 15. The spring 7 is pretensioned with the adjusting nut 9 so that the desired precision (friction of the coupling) can be adjusted. The latching pin 3 of the latching device (1 to 5) latches in one of the bores (2, 2') to set a desired base position of the surgical microscope. The bearing parts are fixed so as to be free of play in a force-tight manner by tightening the fixing nut 10 over the sleeve 11.

It is understood that the foregoing description is that of the preferred embodiments of the invention and that various changes and modifications may be made thereto without departing from the spirit and scope of the invention as defined in the appended claims.

What is claimed is:

1. A coupling for connecting a surgical microscope to a stand so as to permit said microscope to be set in a plurality of base positions relative to said stand, the microscope having a carrier and being pivotable about a pivot axis in each of said base positions, the coupling comprising:

a supporting part for holding said carrier;

a connecting part for connecting said coupling to the stand;

said supporting part having a first bearing part and said connecting part having a second bearing part;

a holder for holding said bearing parts together to conjointly define a bearing and a bearing interface at which said parts rotate relative to each other;

said holder including: a first member connected to one of said bearing parts; a second member engaging said first member for holding said bearing parts together at said interface; and, a biasing device interposed between one of said bearing parts and one of said members to provide a friction force at said interface as said parts are rotated relative to each other;

said biasing device including resilient biasing means for generating a resilient biasing force between said one bearing part and said one member to generate said friction force; and, adjusting means for adjusting said friction force; and, indexing means for indexing said microscope in any one of said base positions.

2. The coupling of claim 1, said indexing means comprising: a plurality of bores formed in said first bearing part defining respective ones of said base positions; and, a latching pin movably mounted between a first position wherein said pin selectively engages any one of said bores and a second position wherein said pin is disengaged from said bore.

3. The coupling of claim 2, said indexing means including a mount for mounting said latching pin; and, a spring interposed between said mount and said latching pin for resiliently biasing said latching pin into the bore.

4. The coupling of claim 1, said one member being said second member; said resilient biasing means being a spring interposed between said second member and said one bearing part; said adjusting means including a thread formed on said first member and an adjusting nut defining said second member threadably engaging said first member on said thread to adjust the tension in said spring when said adjusting nut is rotated to move along said threaded member thereby adjusting said friction force.

5. The coupling of claim 1, further comprising a fixing nut threadably engaging said thread on said first member; and, a sleeve disposed in surrounding relationship to said thread and interposed between one of said parts and said fixing nut so as to permit said first and second bearing parts to be clamped together in a form-tight manner thereby rigidly fixing said microscope in said one base position.

6. The coupling of claim 1, said microscope also being tiltable about a tilt axis in each of said base positions, 7. A coupling for connecting a surgical microscope to a stand so as to permit said microscope to be set in a plurality of base positions relative to said stand, the microscope having a carrier and being pivotable about a pivot axis in each of said base positions, the coupling comprising:

a supporting part for holding said carrier;

a connecting part for connecting said coupling to the stand;

said supporting part having a first bearing part and said connecting part having a second bearing part;

a holder for holding said bearing parts together to conjointly define a bearing and a bearing interface at which said parts rotate relative to each other;

said holder including: a first member connected to one of said bearing parts; a second member engaging said first member for holding said bearing parts together to provide friction force at said interface; and, resilient biasing means interposed between one of said bearing parts and one of said members to determine said friction force;

said holder further including fixing means for fixing said bearing parts in a force-tight manner in any one of said base positions; and, indexing means for indexing said microscope in any one of said base positions.

8. The coupling of claim 7, said fixing means comprising a fixing nut threadably engaging said threaded member; and, a sleeve disposed in surrounding relationship to said threaded member and interposed between one of said parts and said fixing nut so as to permit said first and second bearing parts to be clamped together in said force-tight manner thereby rigidly fixing said microscope in said one base position.

9. A coupling for connecting a surgical microscope to a stand so as to permit said microscope to be set in a plurality of base positions relative to said stand, the microscope having a carrier and being pivotable about a pivot axis in each of said base positions, the coupling comprising:

a supporting part for holding said carrier;

a connecting part for connecting said coupling to the stand;

said supporting part having a first bearing part and said connecting part having a second bearing part;

a holder for holding said bearing parts together to conjointly define a bearing and a bearing interface at which said parts rotate relative to each other;

said holder including: a first member connected to one of said bearing parts; a second member engaging said first member for holding said bearing parts together to provide friction force at said interface; and, resilient biasing means interposed between one of said bearing parts and one of said members to determine said friction force; and, said holder further including fixing means for fixing said bearing parts in a force-tight manner in any one of said base positions.

* * * * *

UNITED STATES PATENT AND TRADEMARK OFFICE
CERTIFICATE OF CORRECTION

PATENT NO. : 5,383,637
DATED     : January 24, 1995
INVENTOR(S) : Klaus Biber

It is certified that error appears in the above-identified patent and that said Letters Patent is hereby corrected as shown below:

In column 3, line 45:  delete "positions," and substitute -- positions. -- therefor.

Signed and Sealed this

Twenty-first Day of March, 1995

Attest:

BRUCE LEHMAN

*Attesting Officer*   *Commissioner of Patents and Trademarks*